(12) United States Patent
Donitzky

(10) Patent No.: US 8,337,489 B2
(45) Date of Patent: Dec. 25, 2012

(54) APPARATUS FOR CUTTING A FLAP IN THE CORNEA OF AN EYE

(75) Inventor: Christof Donitzky, Eckental (DE)

(73) Assignee: Wavelight AG, Erlangen (DE)

( * ) Notice: Subject to any disclaimer, the term of this patent is extended or adjusted under 35 U.S.C. 154(b) by 622 days.

(21) Appl. No.: 12/416,782

(22) Filed: Apr. 1, 2009

(65) Prior Publication Data
US 2010/0256613 A1 Oct. 7, 2010

(51) Int. Cl.
*A61F 9/01* (2006.01)
(52) U.S. Cl. .................................. 606/4; 606/5
(58) Field of Classification Search ............ 606/5, 4
See application file for complete search history.

(56) References Cited

U.S. PATENT DOCUMENTS

| | | | | |
|---|---|---|---|---|
| 6,110,166 | A | * | 8/2000 | Juhasz ............................... 606/5 |
| 6,551,306 | B1 | * | 4/2003 | Carriazo ........................... 606/5 |
| 2003/0055497 | A1 | | 3/2003 | Hicks et al. |
| 2003/0212387 | A1 | | 11/2003 | Kurtz et al. |
| 2004/0243111 | A1 | * | 12/2004 | Bendett et al. ..................... 606/5 |
| 2006/0155265 | A1 | * | 7/2006 | Juhasz et al. ....................... 606/5 |
| 2008/0212623 | A1 | | 9/2008 | Bischoff et al. |

FOREIGN PATENT DOCUMENTS
WO 2007123644 A3 11/2007

OTHER PUBLICATIONS

Nathaniel E. Knox Cartwright et al., "The Biomechanics of Keratorefractive Surgery", CET, May 9, 2008, pp. 30-36, Module 11 Part 9, Course Code: C-8161.
Patent Cooperation Treaty—European Patent Office, "Notification of Transmittal of the International Search Report and the Written Opinion of the International Searching Authority, or the Declaration," International Application No. PCT/EP2009/002382, Oct. 26, 2009, 13 pages.
Cartwright, Nathaniel E. Knox, "The Biomechanics of Keratorefractive Surgery," CET—Continuing Education Training, Sponsored by Johnson & Johnson Vision Care, Model 11, Part 9, Course Code: C-8161, May 9, 2008, pp. 30-36.

* cited by examiner

*Primary Examiner* — Ahmed M Farah
*Assistant Examiner* — Jeffrey Lipitz
(74) *Attorney, Agent, or Firm* — Haynes and Boone, LLP

(57) ABSTRACT

An apparatus for cutting a flap in the cornea of an eye (10) exhibits the following: a laser radiation source for generating laser radiation, means for shaping and guiding the laser radiation in relation to the cornea (20) in such a manner that in the cornea an incision (28) arises which enables a folding of the flap (26) upwards from the cornea. In the process the incision (28) is guided in the hinge region (22) of the cornea in such a way that an undercut arises under the hinge region (22). By this means it is ensured that, in particular in the case of an fs LASIK, the intervention into the stroma is effected substantially symmetrically in relation to a central axis of the cornea (20), so that no undesirable deformations of the cornea result post-operatively by reason of the intraocular pressure.

17 Claims, 3 Drawing Sheets

APPARATUS FOR CUTTING A FLAP IN THE CORNEA OF AN EYE

Figure 1:
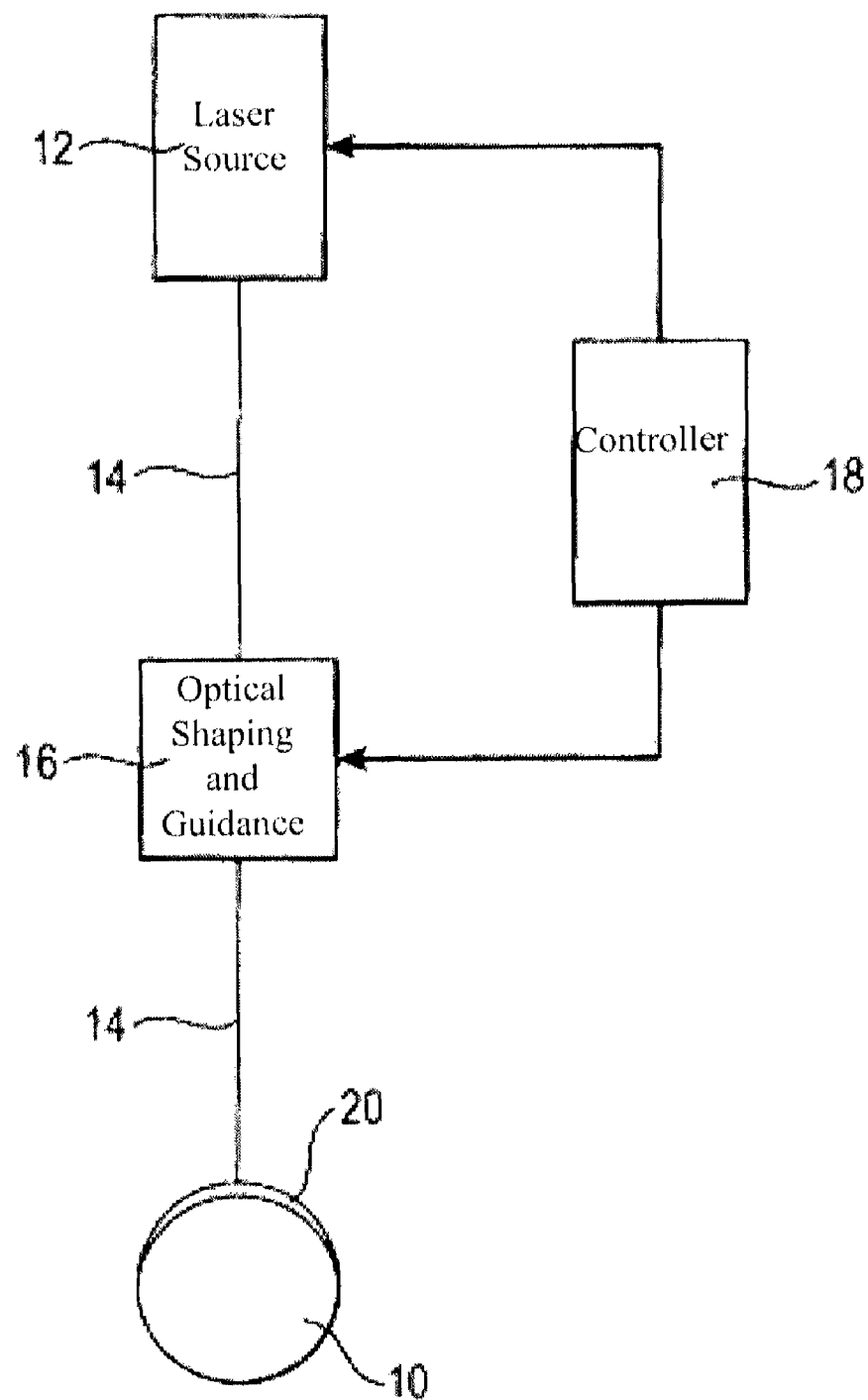

The invention relates to an apparatus for cutting a flap in the cornea of an eye.

In ophthalmological surgery, particularly in the known LASIK process, the term 'flap' has gained acceptance, also in German, for designating a small cover that is cut from the side in an anterior region of the cornea. The flap can then be folded aside, so that in known manner the cornea can be reshaped with laser radiation by ablation for the purpose of eliminating imaging defects.

Currently available for the cutting of such a flap are, on the one hand, the so-called mechanical microkeratome, in which an oscillating blade produces the incision in the cornea, or, on the other hand, so-called femtosecond LASIK, in which a laser is employed having radiation pulses that are set to be so short that the power density of the radiation in the case of focusing in the interior of the cornea brings about so-called photodisruptions therein. By virtue of a control of these femtosecond pulses in space and time an incision in the cornea can then be produced by means of a plurality of such photodisruptions. Nowadays this is a widely known technique.

Both the conventional mechanical microkeratome and the flap incision with femtosecond laser pulses that has been described have the fact in common that a hinge remains at the edge of the flap incision, the term 'hinge' having also been adopted in German. Via such a hinge region, in which the cornea is not severed by the incision, the flap remains connected to the cornea, so that it can be folded back again after implementation of the ablation in the stroma of the cornea.

In the state of the art, such a hinge brings about an asymmetry of the intervention into the cornea in relation to, for example, the optical axis of the eye or another (imaginary) axis perpendicular to the surface of the cornea. The flap incision is not rotationally symmetrical and, in particular, not circular in relation to a central axis of the eye.

After implementation of a LASIK operation, the intraocular pressure of the eye plays a role in the healing process and also in the formation of a corneal shape that cannot be underestimated. By virtue of the photorefractive intervention the biomechanical structure of the eye is changed and therefore the eye can become deformed also after the operation, depending on the altered biomechanical structure. The intraocular pressure deforms the cornea more considerably where it is more weakened.

The asymmetrical guidance of the incision, described above, for the purpose of producing the hinge in the state of the art brings about an asymmetrical configuration of the biomechanical structure of the cornea. After the operation the intraocular pressure can then also bring about an asymmetrical deformation of the cornea by reason of the asymmetrical flap incision, progressing as far as an induced cylinder aberration or aberrations of higher order. In other words: in the state of the art the asymmetrical guidance of the incision in the course of producing the flap can bring about by force an undesirable corneal shape post-operatively by reason of the intraocular pressure.

The object underlying the invention is to make available an apparatus for cutting a flap in the cornea of an eye, wherein the risk of undesirable post-operative deformations of the cornea is diminished.

For this purpose the invention provides an apparatus for cutting a flap in the cornea of an eye, with a laser radiation source for generating laser radiation, means for shaping and guiding the laser radiation in relation to the cornea in such a manner that an incision arises in the cornea, whereby the incision leaves a hinge region in the cornea, via which the flap remains connected to the cornea and which enables a folding of the flap upwards from the cornea, the incision extending under the hinge region with an undercut.

The incision is preferably made substantially symmetrically in such a way that the biomechanical structure of the cornea after the operation is also substantially symmetrical, so that, as far as possible, the intraocular pressure brings about no undesirable 'bulge' on one side of the eye (in relation to the optical axis). In this connection the symmetry is relative to an axis that is perpendicular to the surface of the cornea, in particular—but not necessarily—the optical axis or the visual axis of the eye. If, for the purpose of obtaining an ablation field that is as large as possible, the flap incision is made somewhat asymmetrically in relation to, for example, one of the aforementioned axes (i.e. the spacing of the hinge from the axis is somewhat increased, in order to obtain an ablation field that is as large as possible), the symmetry observations that have been made here relate to such an imaginary axis which is slightly offset in relation to the optical axis or the visual axis.

The flap incision including the undercut under the hinge region that has been described is preferably configured so as to be substantially circular in top view of the eye.

An exemplary embodiment of the invention will be described in more detail in the following on the basis of the drawing.

Figure 2:
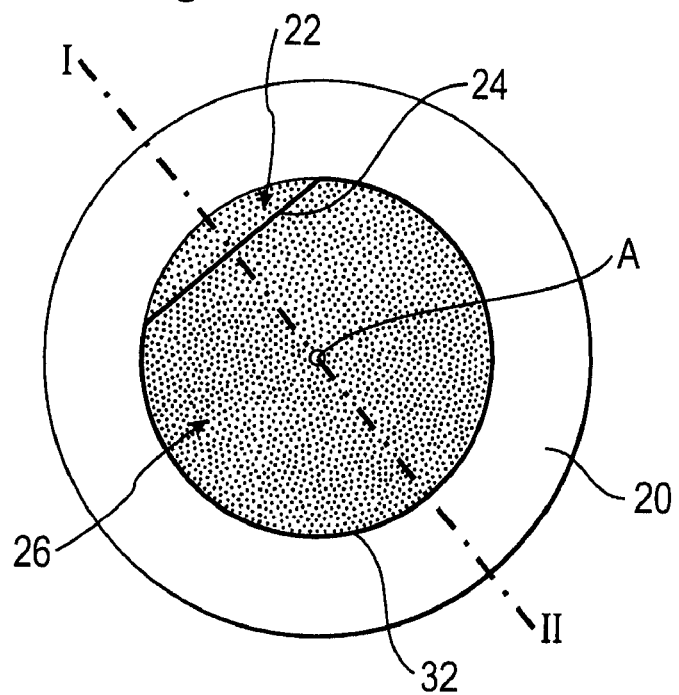
Figure 3:
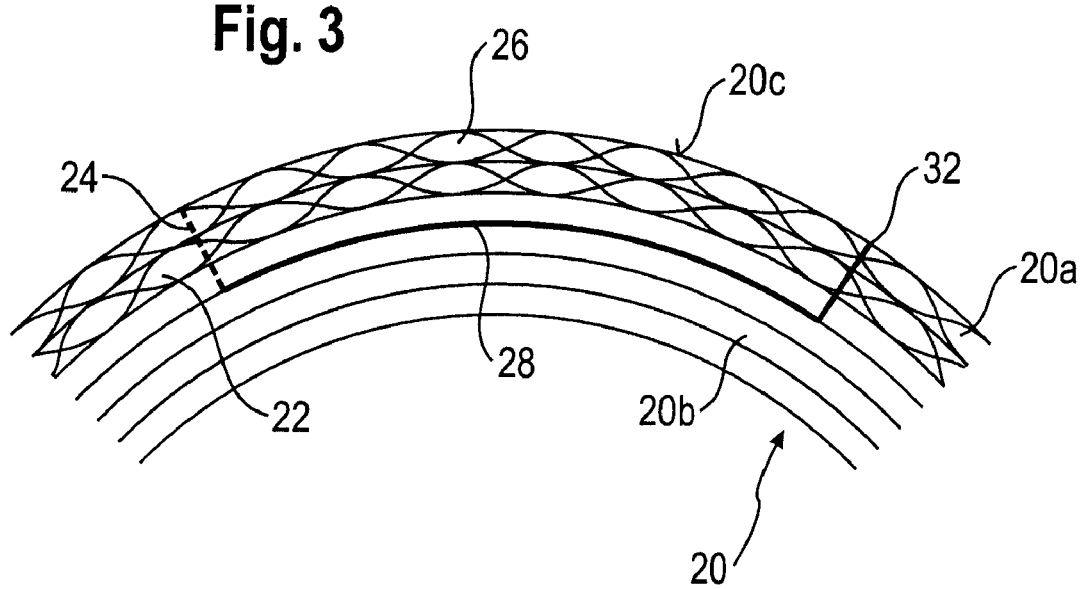
Figure 4:
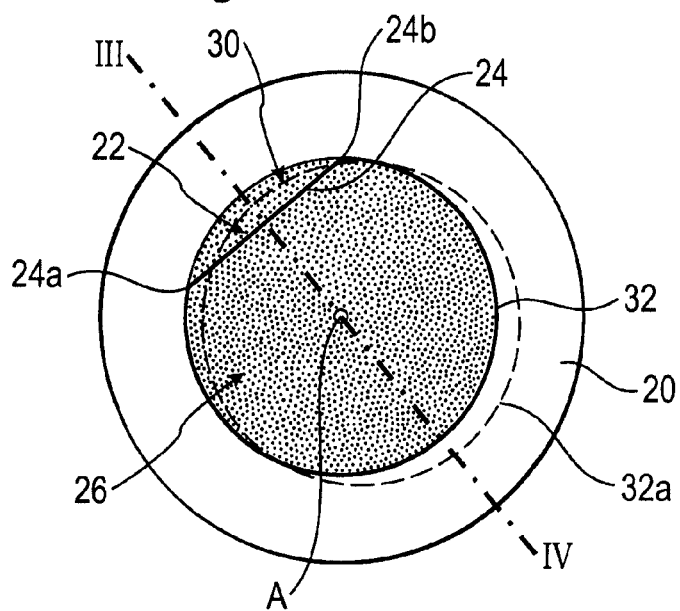
Figure 5:
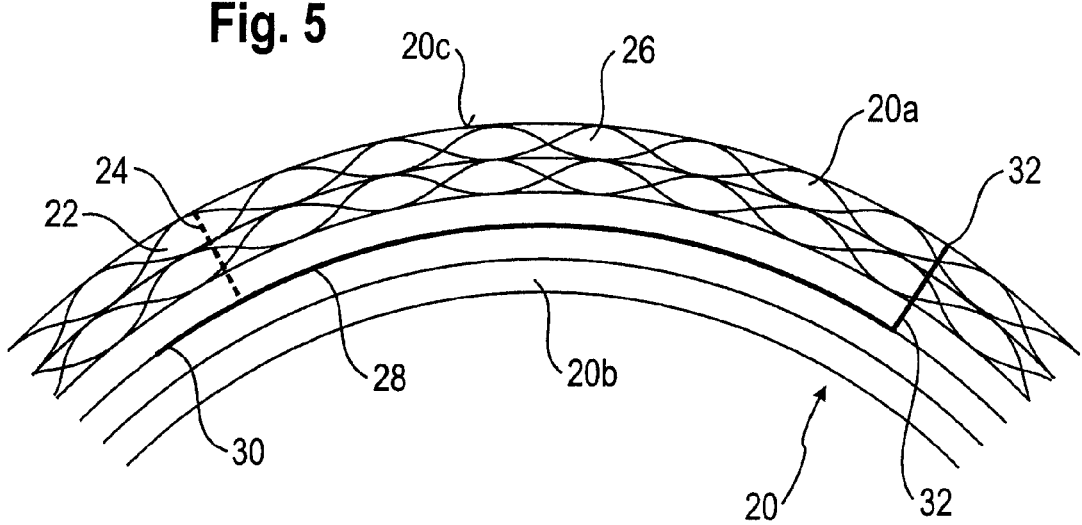

Shown are:

FIG. 1 schematically, an apparatus for cutting a flap in the cornea of an eye;

FIG. 2 an axial top view of the cornea of an eye with incision guidances according to the state of the art;

FIG. 3 a section along line I-II in FIG. 2;

FIG. 4 an axial top view of the cornea of an eye with a flap-incision guidance according to the invention; and FIG. 5 a section along line III-IV in FIG. 4.

FIG. 1 shows schematically the essential components of an apparatus for cutting a flap in the cornea of an eye 10. This apparatus is well-known in principle and therefore does not need to be described further here in all details. As a matter of principle, recourse may be had to a known apparatus of femtosecond LASIK (fs LASIK), and in accordance with the invention a reprogramming of the computer control of the foci of the fs pulses in the cornea is undertaken in novel manner.

The apparatus exhibits a laser radiation source 12 which generates femtosecond laser radiation pulses 14. Means 16 serve for optical shaping and guidance of the laser radiation 14 in relation to the cornea 20 of the eye 10. The optical means required for this purpose and, in particular, the means for controlling the radiation in time and space (scanner etc.) are well-known. A computer controller 18 controls both the laser radiation source 12 and the means 16 for the shaping and guidance of the radiation.

FIGS. 2 and 3 illustrate the problems in the state of the art. FIG. 2 shows a top view of the cornea 20 in the axial direction. FIG. 3 shows the incision along line I-II in FIG. 2.

In the case of the photodisruptively produced incision 28 a hinge region 22 remains in known manner, via which the flap 26 remains connected to the cornea 20. The edge of the hinge region 22 is denoted in the Figures by 24. In the state of the art the flap 26 is accordingly folded upwards at this edge 24. In the state of the art the incision 28 terminates at the edge 24—that is to say, it does not extend under the hinge region 22. On the opposite side the marginal incision 32 is guided upwards in known manner to the surface 20c of the cornea.

Since in FIGS. 2 and 3 the incision terminates at the edge 24, an asymmetrical configuration of the biomechanical properties of the cornea arises in relation to a central axis A. In the hinge region 22 the cornea is weakened less than in those regions in which the incision 28 is guided. FIG. 3 show schematically the epithelial region 20a and the stromal region 20b of the cornea 20. The epithelium of the cornea has a microstructure differing from that of the stroma. The latter exhibits so-called lamellae which extend parallel to the corneal surface. These lamellae substantially establish the biomechanical stability of the cornea. An incision through the lamellae consequently constitutes a considerable intervention into the biomechanical structure and symmetry of the formal structure constituted by the eye. Therefore after implementation of an operation with asymmetrical incision guidance according to FIGS. 2 and 3 the radially acting intraocular pressure may bring about post-operatively a deformation of the cornea that is not precisely foreseeable, particularly when the ablative intervention extends relatively far and weakens the stroma.

Such a risk of an undesirable post-operative deformation of the cornea is avoided with the incision guidance illustrated in FIGS. 4 and 5. In the Figures, parts and components that are functionally similar to one another have been provided with the same reference symbols. FIG. 5 is a section along line III-IV in FIG. 4. According to FIGS. 4 and 5, the incision 28 generated photodisruptively with femtosecond pulses does not terminate at the edge 24 of the hinge region 22 but is guided below the hinge region 22 in the form of an undercut 30 beyond the edge 24. Accordingly, no incision takes place at the edge 24, the dotted representation is only an imaginary line (similarly in FIG. 3). At the two end points 24a, 24b the connection between the flap 26 and the cornea 30 is consequently preserved, and these two end points 24a, 24b consequently define a hinge line along which the flap 26 is folded upwards. With the flap 26 folded upwards, the undercut 30 accordingly remains below the hinge region 22 which has remained intact. Stroma for the subsequent ablative treatment is exposed, just as in the state of the art illustrated above.

But, otherwise than in the state of the art that has been described, the undercut 30 of the photodisruptive incision brings about a substantially more symmetrical intervention in relation to a central axis A of the eye, with the advantages described above.

FIG. 4 shows with reference symbol 32a a modification of the exemplary embodiment described above. In this modification the flap 26 is not precisely concentric in relation to the centre of an eye feature such as, for example, a pupil. According to this modification, it is taken into account that the hinge region, via which the flap remains connected to the cornea, gives rise to a restriction of the region of the cornea that is available for the laser ablation. The hinge region cannot be used for the laser ablation. Therefore, according to this variant of the invention, the perimeter of the flap is not chosen to be concentric in relation to the pupil of the eye. For the purpose of obtaining a maximal ablation zone, the perimeter of the flap incision is offset in relation to the pupillary centre, specifically away from the edge 24 of the hinge region 22. This is indicated in FIG. 4 by the dashed line 32a, which indicates schematically a flap perimeter that has been offset in such a manner.

The invention claimed is:

1. Apparatus for cutting a flap in the cornea of an eye, comprising:
   a laser radiation source for generating laser radiation;
   means for shaping and guiding the laser radiation in relation to the cornea in such a manner that:
      in the cornea an incision arises;
      whereby, an epithelium portion of the incision leaves a hinge region in the epithelium of the cornea, via which the flap remains connected to the cornea and which enables a folding of the flap upwards from the cornea;
      wherein, a stromal portion of the incision has a circular profile within the stroma of the cornea such that a section of the circular stromal portion of the incision extends under the hinge region to define an undercut.

2. Apparatus according to claim 1, characterized in that the incision is substantially symmetrical in relation to an axis which is perpendicular to the corneal surface.

3. Apparatus according to claim 2, characterized in that the incision is substantially circular.

4. Apparatus according to claim 1, characterized in that the incision is acentric in relation to a center of a pupil of the eye.

5. Method for cutting a flap in the cornea of an eye, the method comprising:
   providing a laser radiation source for generating laser radiation;
   shaping and guiding the laser radiation in relation to the cornea in such a manner that in the cornea an incision arises, whereby the incision leaves a hinge region in an epithelium of the cornea, via which the flap remains connected to the cornea and which enables a folding of the flap upwards from the cornea; and,
   generating a circular incision within the stroma such that an undercut is formed under the hinge region in the epithelium.

6. Method according to claim 5, wherein the incision is substantially symmetrical in relation to an axis which is perpendicular to the corneal surface.

7. Method according to claim 6, characterized in that the incision, including the stated undercut, is substantially circular.

8. Method according to claim 7, wherein a majority of an outer boundary of the flap is substantially circular.

9. Method according to claim 8, wherein a hinge line extends between end points of the substantially circular majority of the outer boundary of the flap.

10. Method according to claim 9, further comprising:
    folding the flap upwards to expose a stroma; and
    ablating the stroma.

11. Method according to claim 5, wherein the incision is offset relative to a central axis of the eye.

12. Method according to claim 11, wherein the incision, including the stated undercut, is substantially circular.

13. Method according to claim 12, wherein a hinge line extends between end points of the substantially circular majority of the outer boundary of the flap.

14. Method according to claim 13, further comprising:
    folding the flap upwards to expose a stroma; and
    ablating the stroma.

15. A system for cutting a flap in a cornea of an eye, comprising:
    a laser radiation source for generating laser radiation;
    a controller in communication with the laser radiation source, the controller configured to control application of the generated laser radiation to the eye the laser radiation source such that:
       an incision is formed in the cornea of the eye such that a first portion of the incision defines a flap and a hinge region in the epithelium of the cornea and a second portion of the incision defines a circular incision within a stroma of the cornea such that an undercut is formed in the stroma of the cornea underneath the hinge region in the epithelium.

16. The system of claim 15, wherein a majority of an outer boundary of the flap is circular.

17. The system of claim 16, wherein a hinge line extends between end points of the substantially circular majority of the outer boundary of the flap, the hinge line representing a boundary between the hinge region and the flap.

* * * * *